United States Patent
Uribe

(10) Patent No.: US 9,060,813 B1
(45) Date of Patent: Jun. 23, 2015

(54) SURGICAL FIXATION SYSTEM AND RELATED METHODS

(71) Applicant: NuVasive, Inc., San Diego, CA (US)

(72) Inventor: Juan S. Uribe, Tampa, FL (US)

(73) Assignee: NuVasive, Inc., San Diego, CA (US)

( * ) Notice: Subject to any disclaimer, the term of this patent is extended or adjusted under 35 U.S.C. 154(b) by 172 days.

(21) Appl. No.: 13/647,331

(22) Filed: Oct. 8, 2012

Related U.S. Application Data

(63) Continuation of application No. 13/453,885, filed on Apr. 23, 2012, now abandoned, which is a continuation of application No. 13/315,082, filed on Dec. 8, 2011, now abandoned, which is a continuation of application No. 13/185,434, filed on Jul. 18, 2011, now abandoned, which is a continuation of application No. 13/037,194, filed on Feb. 28, 2011, now abandoned, which is a continuation of application No. 12/906,685, filed on Oct. 18, 2010, now abandoned, which is a continuation of application No. 12/794,016, filed on Jun. 4, 2010, now abandoned, which is a continuation of application No. 12/581,790, filed on Oct. 19, 2009, now abandoned, which is a continuation of application No. 12/396,332, filed on Mar. 2, 2009, now abandoned.

(60) Provisional application No. 61/032,768, filed on Feb. 29, 2008.

(51) Int. Cl.
| | |
|---|---|
| *A61B 17/88* | (2006.01) |
| *A61B 17/70* | (2006.01) |
| *A61B 17/56* | (2006.01) |

(52) U.S. Cl.
CPC ......... *A61B 17/7037* (2013.01); *A61B 17/7032* (2013.01); *A61B 2017/564* (2013.01); *A61B 17/7035* (2013.01); *A61B 17/88* (2013.01); *A61B 17/7001* (2013.01)

(58) Field of Classification Search
CPC ............... A61B 17/88; A61B 17/7035; A61B 17/7001; A61B 17/7032; A61B 2017/564
USPC .................................................. 606/264, 279
See application file for complete search history.

(56) References Cited

U.S. PATENT DOCUMENTS

| | | | |
|---|---|---|---|
| 929,067 | A | 7/1909 | Williamson |
| 1,841,647 | A | 1/1932 | Smith |
| 3,367,326 | A | 2/1968 | Frazier |
| 3,610,092 | A | 10/1971 | Miller |
| 4,361,141 | A | 11/1982 | Tanner |
| 4,414,966 | A | 11/1983 | Stednitz |

(Continued)

FOREIGN PATENT DOCUMENTS

| | | |
|---|---|---|
| AU | 723894 | 12/1998 |
| BR | PI108011303 | 6/2011 |

(Continued)

OTHER PUBLICATIONS

Beadling, "Harrington put the steel in spinal fixation", Orthopedics Today, (Jun. 2000), 6 pgs.

(Continued)

*Primary Examiner* — Ellen C Hammond
(74) *Attorney, Agent, or Firm* — Jonathan Spangler; Jennifer Russell

(57) ABSTRACT

Occipital-cervical stabilization using occipital condyle fixation with a polyaxial screw-rod construct.

12 Claims, 4 Drawing Sheets

(56) References Cited

U.S. PATENT DOCUMENTS

| | | |
|---|---|---|
| 4,484,570 A | 11/1984 | Sutter |
| 4,537,185 A | 8/1985 | Stednitz |
| 4,569,338 A | 2/1986 | Edwards |
| 4,577,837 A | 3/1986 | Berg |
| 4,641,636 A | 2/1987 | Cotrel |
| 4,648,388 A | 3/1987 | Steffee |
| 4,771,767 A | 9/1988 | Steffee |
| 4,805,602 A | 2/1989 | Puno |
| 4,946,458 A | 8/1990 | Harms |
| 4,998,936 A | 3/1991 | Mehdian |
| 5,002,542 A | 3/1991 | Frigg |
| 5,005,562 A | 4/1991 | Cotrel |
| 5,024,213 A | 6/1991 | Asher |
| 5,034,011 A | 7/1991 | Howland |
| 5,042,982 A | 8/1991 | Harms |
| 5,047,029 A | 9/1991 | Aebi |
| 5,084,049 A | 1/1992 | Asher |
| 5,092,866 A | 3/1992 | Breard |
| 5,092,867 A | 3/1992 | Harms |
| 5,092,893 A | 3/1992 | Smith |
| 5,129,388 A | 7/1992 | Vignaud |
| 5,154,718 A | 10/1992 | Cozad |
| 5,176,680 A | 1/1993 | Vignaud |
| 5,196,013 A | 3/1993 | Harms |
| 5,207,678 A | 5/1993 | Harms |
| 5,209,752 A | 5/1993 | Ashman |
| 5,217,461 A | 6/1993 | Asher |
| 5,234,431 A | 8/1993 | Keller |
| 5,261,907 A | 11/1993 | Sacriste |
| 5,275,600 A | 1/1994 | Allard |
| 5,288,161 A | 2/1994 | Graves |
| 5,312,405 A | 5/1994 | Korotko |
| 5,318,388 A | 6/1994 | Papadopoulos |
| 5,330,473 A | 7/1994 | Howland |
| 5,332,330 A | 7/1994 | Kaneko |
| 5,360,429 A | 11/1994 | Jeanson |
| 5,375,823 A | 12/1994 | Navas |
| 5,380,323 A | 1/1995 | Howland |
| 5,387,213 A | 2/1995 | Breard |
| 5,397,363 A | 3/1995 | Gelbard |
| 5,403,314 A | 4/1995 | Currier |
| 5,443,467 A | 8/1995 | Biedermann |
| 5,466,237 A | 11/1995 | Byrd |
| 5,474,555 A | 12/1995 | Puno |
| 5,476,464 A | 12/1995 | Metz-Stavenhagen |
| 5,478,340 A | 12/1995 | Kluger |
| 5,480,401 A | 1/1996 | Navas |
| 5,498,263 A | 3/1996 | Dinello |
| 5,501,684 A | 3/1996 | Schlapfer |
| 5,505,731 A | 4/1996 | Tornier |
| 5,507,745 A | 4/1996 | Logroscino |
| 5,522,816 A | 6/1996 | Dinello |
| 5,536,268 A | 7/1996 | Griss |
| 5,540,688 A | 7/1996 | Navas |
| 5,542,946 A | 8/1996 | Logroscino |
| 5,545,163 A | 8/1996 | Miller |
| 5,545,164 A | 8/1996 | Howland |
| 5,545,166 A | 8/1996 | Howland |
| 5,549,608 A | 8/1996 | Errico |
| 5,558,674 A | 9/1996 | Heggeness |
| 5,562,661 A | 10/1996 | Yoshimi |
| 5,569,246 A | 10/1996 | Ojima |
| 5,575,791 A | 11/1996 | Lin |
| 5,584,831 A | 12/1996 | Mckay |
| 5,593,408 A | 1/1997 | Gayet |
| 5,601,554 A | 2/1997 | Howland |
| 5,607,425 A | 3/1997 | Rogozinski |
| 5,609,593 A | 3/1997 | Errico |
| 5,624,442 A | 4/1997 | Mellinger |
| 5,630,816 A | 5/1997 | Kambin |
| 5,643,264 A | 7/1997 | Sherman |
| 5,645,544 A | 7/1997 | Tai |
| 5,653,708 A | 8/1997 | Howland |
| 5,665,122 A | 9/1997 | Kambin |
| 5,667,508 A | 9/1997 | Errico |
| 5,669,910 A | 9/1997 | Korhonen |
| 5,669,911 A | 9/1997 | Errico |
| 5,672,176 A | 9/1997 | Harms |
| 5,676,665 A | 10/1997 | Bryan |
| 5,676,703 A | 10/1997 | Gelbard |
| 5,681,311 A | 10/1997 | Foley |
| 5,681,319 A | 10/1997 | Biedermann |
| 5,688,272 A | 11/1997 | Montague |
| 5,690,630 A | 11/1997 | Errico |
| 5,693,053 A | 12/1997 | Estes |
| 5,697,929 A | 12/1997 | Mellinger |
| 5,702,393 A | 12/1997 | Pfaifer |
| 5,704,936 A | 1/1998 | Mazel |
| 5,714,255 A | 2/1998 | Yeh |
| 5,716,355 A | 2/1998 | Jackson |
| 5,725,527 A | 3/1998 | Biedermann |
| 5,728,097 A | 3/1998 | Mathews |
| 5,728,098 A | 3/1998 | Sherman |
| 5,735,851 A | 4/1998 | Errico |
| 5,735,852 A | 4/1998 | Amrein |
| 5,741,255 A | 4/1998 | Glascott |
| 5,752,957 A | 5/1998 | Ralph |
| 5,776,135 A | 7/1998 | Errico |
| 5,782,831 A | 7/1998 | Sherman |
| 5,800,435 A | 9/1998 | Errico |
| 5,810,818 A | 9/1998 | Errico |
| 5,816,633 A | 10/1998 | Odom |
| 5,863,293 A | 1/1999 | Richelsoph |
| 5,873,878 A | 2/1999 | Harms |
| 5,879,350 A | 3/1999 | Sherman |
| 5,885,286 A | 3/1999 | Sherman |
| 5,891,145 A | 4/1999 | Morrison |
| 5,928,232 A | 7/1999 | Howland |
| 5,928,237 A | 7/1999 | Farris |
| 5,938,663 A | 8/1999 | Petreto |
| 5,944,719 A | 8/1999 | Leban |
| 5,944,720 A | 8/1999 | Lipton |
| 5,947,966 A | 9/1999 | Drewry |
| 5,951,555 A | 9/1999 | Rehak |
| 5,954,722 A | 9/1999 | Bono |
| 5,954,725 A | 9/1999 | Sherman |
| 5,961,516 A | 10/1999 | Graf |
| 5,964,769 A | 10/1999 | Wagner |
| 5,976,135 A | 11/1999 | Sherman |
| 5,980,521 A | 11/1999 | Montague |
| 5,980,523 A | 11/1999 | Jackson |
| 6,004,322 A | 12/1999 | Bernstein |
| 6,004,349 A | 12/1999 | Jackson |
| 6,030,389 A | 2/2000 | Wagner |
| 6,063,089 A | 5/2000 | Errico |
| 6,063,090 A | 5/2000 | Schlapfer |
| 6,074,391 A | 6/2000 | Metz-Stavenhagen |
| 6,083,226 A | 7/2000 | Fiz |
| 6,106,526 A | 8/2000 | Harms |
| 6,113,600 A | 9/2000 | Drummond |
| 6,113,601 A | 9/2000 | Tatar |
| 6,123,706 A | 9/2000 | Lange |
| 6,132,432 A | 10/2000 | Richelsoph |
| 6,136,003 A | 10/2000 | Drummond |
| 6,139,548 A | 10/2000 | Errico |
| 6,171,311 B1 | 1/2001 | Richelsoph |
| 6,174,110 B1 | 1/2001 | Papadopoulos |
| 6,179,838 B1 | 1/2001 | Fiz |
| 6,183,473 B1 | 2/2001 | Ashman |
| 6,187,005 B1 | 2/2001 | Brace |
| 6,190,388 B1 | 2/2001 | Michelson |
| 6,210,413 B1 | 4/2001 | Sherman |
| 6,217,578 B1 | 4/2001 | Crozet |
| 6,224,596 B1 | 5/2001 | Jackson |
| 6,224,598 B1 | 5/2001 | Jackson |
| 6,231,575 B1 | 5/2001 | Krag |
| 6,234,705 B1 | 5/2001 | Troxell |
| 6,235,033 B1 | 5/2001 | Brace |
| 6,238,396 B1 | 5/2001 | Lombardo |
| 6,241,730 B1 | 6/2001 | Alby |
| 6,248,105 B1 | 6/2001 | Schläpfer |
| 6,251,112 B1 | 6/2001 | Jackson |
| 6,254,532 B1 | 7/2001 | Paolitto |
| 6,258,090 B1 | 7/2001 | Jackson |

(56) References Cited

U.S. PATENT DOCUMENTS

| | | |
|---|---|---|
| 6,261,288 B1 | 7/2001 | Jackson |
| 6,261,291 B1 | 7/2001 | Talaber |
| 6,264,658 B1 | 7/2001 | Lee |
| 6,267,765 B1 | 7/2001 | Taylor |
| 6,273,914 B1 | 8/2001 | Papas |
| 6,280,422 B1 | 8/2001 | Sanchez-Browning |
| 6,280,442 B1 | 8/2001 | Barker |
| 6,280,445 B1 | 8/2001 | Johnson |
| 6,283,967 B1 | 9/2001 | Kumar |
| 6,296,644 B1 | 10/2001 | Saurat |
| 6,306,137 B2 | 10/2001 | Troxell |
| 6,325,802 B1 | 12/2001 | Frigg |
| 6,328,740 B1 | 12/2001 | Richelsoph |
| 6,328,741 B1 | 12/2001 | Richelsoph |
| 6,379,354 B1 | 4/2002 | Rogozinski |
| 6,402,749 B1 | 6/2002 | Ashman |
| 6,402,751 B1 | 6/2002 | Hoeck |
| 6,413,258 B1 | 7/2002 | Bernhardt |
| 6,454,773 B1 | 9/2002 | Sherman |
| 6,471,703 B1 | 10/2002 | Ashman |
| 6,482,207 B1 | 11/2002 | Errico |
| 6,485,491 B1 | 11/2002 | Farris |
| 6,485,494 B1 | 11/2002 | Haider |
| 6,488,681 B2 | 12/2002 | Martin |
| 6,520,962 B1 | 2/2003 | Taylor |
| 6,524,310 B1 | 2/2003 | Lombardo |
| 6,524,315 B1 | 2/2003 | Selvitelli |
| 6,547,790 B2 | 4/2003 | Harkey |
| 6,554,832 B2 | 4/2003 | Shluzas |
| 6,554,834 B1 | 4/2003 | Crozet |
| 6,575,975 B2 | 6/2003 | Brace |
| 6,602,253 B2 | 8/2003 | Usher |
| 6,616,668 B2 | 9/2003 | Altarac |
| 6,623,485 B2 | 9/2003 | Doubler |
| 6,626,904 B1 | 9/2003 | Jammet |
| 6,626,906 B1 | 9/2003 | Young |
| 6,641,583 B2 | 11/2003 | Shluzas |
| 6,648,887 B2 | 11/2003 | Ashman |
| 6,660,004 B2 | 12/2003 | Barker |
| 6,685,705 B1 | 2/2004 | Taylor |
| 6,716,214 B1 | 4/2004 | Jackson |
| 6,719,759 B2 | 4/2004 | Wagner |
| 6,736,817 B2 | 5/2004 | Troxell |
| 6,736,820 B2 | 5/2004 | Biedermann |
| 6,752,807 B2 | 6/2004 | Lin |
| 6,755,830 B2 | 6/2004 | Minfelde |
| 6,761,721 B2 | 7/2004 | Burgess |
| 6,783,526 B1 | 8/2004 | Lin |
| 6,802,844 B2 | 10/2004 | Ferree |
| 6,835,196 B2 | 12/2004 | Biedermann |
| 6,837,889 B2 | 1/2005 | Shluzas |
| 6,858,030 B2 | 2/2005 | Martin |
| 6,872,208 B1 | 3/2005 | Mcbride |
| 6,872,209 B2 | 3/2005 | Morrison |
| 6,875,211 B2 | 4/2005 | Nichols |
| 6,887,241 B1 | 5/2005 | Mcbride |
| 6,890,334 B2 | 5/2005 | Brace |
| 6,899,714 B2 | 5/2005 | Vaughan |
| 6,902,565 B2 | 6/2005 | Berger |
| 6,958,066 B2 | 10/2005 | Richelsoph |
| 6,960,212 B2 | 11/2005 | Richelsoph |
| 6,964,666 B2 | 11/2005 | Jackson |
| 6,974,460 B2 | 12/2005 | Carbone |
| 7,022,122 B2 | 4/2006 | Amrein |
| 7,029,474 B2 | 4/2006 | Richelsoph |
| 7,066,938 B2 | 6/2006 | Slivka |
| 7,066,939 B2 | 6/2006 | Taylor |
| RE39,235 E | 8/2006 | Shuler et al. |
| 7,083,621 B2 | 8/2006 | Shaolian |
| 7,083,622 B2 | 8/2006 | Simonson |
| 7,087,057 B2 | 8/2006 | Konieczynski |
| 7,104,993 B2 | 9/2006 | Baynham |
| 7,122,036 B2 | 10/2006 | Vanacker |
| 7,137,986 B2 | 11/2006 | Troxell |
| 7,160,301 B2 | 1/2007 | Cordaro |
| 7,163,539 B2 | 1/2007 | Abdelgany |
| 7,179,261 B2 | 2/2007 | Sicvol |
| 7,186,255 B2 | 3/2007 | Baynham |
| 7,204,853 B2 | 4/2007 | Gordon |
| 7,211,087 B2 | 5/2007 | Young |
| 7,223,268 B2 | 5/2007 | Biedermann |
| 7,250,052 B2 | 7/2007 | Landry |
| 7,264,621 B2 | 9/2007 | Coates |
| 7,377,923 B2 | 5/2008 | Purcell |
| 7,406,775 B2 | 8/2008 | Funk |
| 7,476,239 B2 | 1/2009 | Jackson |
| 7,530,992 B2 | 5/2009 | Biedermann |
| 7,625,033 B2 | 12/2009 | Michelau |
| 7,635,380 B2 | 12/2009 | Zucherman |
| 7,666,189 B2 | 2/2010 | Gerber et al. |
| 7,678,112 B2 | 3/2010 | Rezach |
| 7,678,137 B2 | 3/2010 | Butler |
| 7,727,261 B2 | 6/2010 | Barker |
| 7,731,736 B2 | 6/2010 | Guenther |
| 7,785,354 B2 | 8/2010 | Biedermann |
| 7,819,902 B2 | 10/2010 | Abdelgany |
| 7,857,834 B2 | 12/2010 | Boschert |
| 7,862,588 B2 | 1/2011 | Abdou |
| 7,909,830 B2 | 3/2011 | Frigg |
| 7,914,558 B2 | 3/2011 | Landry |
| 7,947,065 B2 | 5/2011 | Hammill |
| 7,955,358 B2 | 6/2011 | Albert |
| 7,955,364 B2 | 6/2011 | Ziolo |
| 7,985,242 B2 | 7/2011 | Forton |
| 8,002,806 B2 | 8/2011 | Justis |
| 8,012,177 B2 | 9/2011 | Jackson |
| 8,012,181 B2 | 9/2011 | Winslow |
| 8,021,397 B2 | 9/2011 | Farris |
| 8,021,398 B2 | 9/2011 | Sweeney |
| 8,034,084 B2 | 10/2011 | Landry |
| 8,043,341 B2 | 10/2011 | Zhao |
| 8,062,339 B2 | 11/2011 | Hammer |
| 8,100,916 B2 | 1/2012 | Kumar |
| 8,100,946 B2 | 1/2012 | Strausbaugh |
| 8,162,990 B2 | 4/2012 | Potash |
| 8,167,915 B2 | 5/2012 | Ferree |
| 8,172,847 B2 | 5/2012 | Dziedzic |
| 8,221,472 B2 | 7/2012 | Peterson |
| 8,241,341 B2 | 8/2012 | Walker |
| 8,277,490 B2 | 10/2012 | Freeman |
| 8,308,774 B2 | 11/2012 | Hoffman |
| 8,506,601 B2 | 8/2013 | Gephart |
| 2001/0034521 A1 | 10/2001 | Bailey |
| 2002/0052603 A1 | 5/2002 | Nichols |
| 2002/0058942 A1 | 5/2002 | Biedermann |
| 2002/0120268 A1 | 8/2002 | Berger |
| 2002/0143330 A1 | 10/2002 | Shluzas |
| 2002/0169448 A1 | 11/2002 | Vanacker |
| 2002/0173789 A1 | 11/2002 | Howland |
| 2003/0023244 A1 | 1/2003 | Richelsoph |
| 2003/0023564 A1 | 1/2003 | Padhye |
| 2003/0028191 A1 | 2/2003 | Shluzas |
| 2003/0045878 A1 | 3/2003 | Petit |
| 2003/0100896 A1 | 5/2003 | Biedermann |
| 2003/0149432 A1 | 8/2003 | Frigg |
| 2003/0153913 A1 | 8/2003 | Altarac |
| 2003/0153917 A1 | 8/2003 | Richelsoph |
| 2003/0163133 A1 | 8/2003 | Altarac |
| 2003/0212398 A1 | 11/2003 | Jackson |
| 2003/0225408 A1 | 12/2003 | Nichols |
| 2004/0116928 A1 | 6/2004 | Young |
| 2004/0138662 A1 | 7/2004 | Landry |
| 2004/0143265 A1 | 7/2004 | Landry |
| 2004/0147928 A1 | 7/2004 | Landry |
| 2004/0153070 A1 | 8/2004 | Barker |
| 2004/0153077 A1 | 8/2004 | Biedermann |
| 2004/0172022 A1 | 9/2004 | Landry |
| 2004/0243126 A1 | 12/2004 | Carbone |
| 2004/0260284 A1 | 12/2004 | Parker |
| 2004/0260287 A1 | 12/2004 | Ferree |
| 2005/0010217 A1 | 1/2005 | Dalton |
| 2005/0070901 A1 | 3/2005 | David |
| 2005/0080415 A1 | 4/2005 | Keyer |
| 2005/0080416 A1 | 4/2005 | Ryan |

(56) References Cited

U.S. PATENT DOCUMENTS

| | | |
|---|---|---|
| 2005/0080417 A1 | 4/2005 | Alexis |
| 2005/0080420 A1 | 4/2005 | Farris |
| 2005/0085813 A1 | 4/2005 | Spitler |
| 2005/0090821 A1 | 4/2005 | Berrevoets |
| 2005/0101954 A1 | 5/2005 | Simonson |
| 2005/0113927 A1 | 5/2005 | Malek |
| 2005/0124994 A1 | 6/2005 | Berger |
| 2005/0137594 A1 | 6/2005 | Doubler |
| 2005/0154391 A1 | 7/2005 | Doherty |
| 2005/0154393 A1 | 7/2005 | Doherty |
| 2005/0182409 A1 | 8/2005 | Callahan |
| 2005/0192572 A1 | 9/2005 | Abdelgany |
| 2005/0203515 A1 | 9/2005 | Doherty |
| 2005/0228326 A1 | 10/2005 | Kalfas |
| 2005/0228382 A1 | 10/2005 | Richelsoph |
| 2005/0240181 A1 | 10/2005 | Boomer |
| 2005/0261690 A1 | 11/2005 | Binder |
| 2005/0277923 A1 | 12/2005 | Sweeney |
| 2005/0277927 A1 | 12/2005 | Guenther |
| 2005/0277928 A1 | 12/2005 | Boschert |
| 2005/0288670 A1 | 12/2005 | Panjabi |
| 2006/0025771 A1 | 2/2006 | Jackson |
| 2006/0036244 A1 | 2/2006 | Spitler |
| 2006/0036252 A1 | 2/2006 | Baynham |
| 2006/0052783 A1 | 3/2006 | Dant |
| 2006/0052786 A1 | 3/2006 | Dant |
| 2006/0058787 A1 | 3/2006 | David |
| 2006/0058789 A1 | 3/2006 | Kim |
| 2006/0060823 A1 | 3/2006 | Cooke |
| 2006/0064091 A1 | 3/2006 | Ludwig |
| 2006/0064093 A1 | 3/2006 | Thramann |
| 2006/0084978 A1 | 4/2006 | Mokhtar |
| 2006/0084979 A1 | 4/2006 | Jackson |
| 2006/0084993 A1 | 4/2006 | Khoo |
| 2006/0084995 A1 | 4/2006 | Biedermann |
| 2006/0089651 A1 | 4/2006 | Trudeau |
| 2006/0095035 A1 | 5/2006 | Jones |
| 2006/0095038 A1 | 5/2006 | Jackson |
| 2006/0100622 A1 | 5/2006 | Jackson |
| 2006/0111712 A1 | 5/2006 | Jackson |
| 2006/0111713 A1 | 5/2006 | Jackson |
| 2006/0111714 A1 | 5/2006 | Foley |
| 2006/0111715 A1 | 5/2006 | Jackson |
| 2006/0122604 A1 | 6/2006 | Gorhan |
| 2006/0142761 A1 | 6/2006 | Landry |
| 2006/0149229 A1 | 7/2006 | Kwak |
| 2006/0149232 A1 | 7/2006 | Sasing |
| 2006/0149233 A1 | 7/2006 | Richelsoph |
| 2006/0149240 A1 | 7/2006 | Jackson |
| 2006/0155277 A1 | 7/2006 | Metz-Stavenhagen |
| 2006/0155283 A1 | 7/2006 | Doherty |
| 2006/0155284 A1 | 7/2006 | Doherty |
| 2006/0161153 A1 | 7/2006 | Hawkes |
| 2006/0167454 A1 | 7/2006 | Ludwig |
| 2006/0173454 A1 | 8/2006 | Spitler |
| 2006/0173456 A1 | 8/2006 | Hawkes |
| 2006/0179244 A1 | 8/2006 | Goodman |
| 2006/0200133 A1 | 9/2006 | Jackson |
| 2006/0200136 A1 | 9/2006 | Jackson |
| 2006/0217710 A1 | 9/2006 | Abdou |
| 2006/0217718 A1 | 9/2006 | Chervitz |
| 2006/0217725 A1 | 9/2006 | Suh |
| 2006/0217735 A1 | 9/2006 | Macdonald |
| 2006/0229606 A1 | 10/2006 | Clement |
| 2006/0229610 A1 | 10/2006 | Piehl |
| 2006/0235393 A1 | 10/2006 | Bono |
| 2006/0241599 A1 | 10/2006 | Konieczynski |
| 2006/0241601 A1 | 10/2006 | Trautwein |
| 2006/0241603 A1 | 10/2006 | Jackson |
| 2006/0247624 A1 | 11/2006 | Banouskou |
| 2006/0247631 A1 | 11/2006 | Ahn |
| 2006/0264933 A1 | 11/2006 | Baker |
| 2006/0271045 A1 | 11/2006 | Hubbard |
| 2006/0271047 A1 | 11/2006 | Jackson |
| 2006/0271050 A1 | 11/2006 | Piza Vallespir |
| 2006/0276789 A1 | 12/2006 | Jackson |
| 2006/0276792 A1 | 12/2006 | Ensign |
| 2006/0282074 A1 | 12/2006 | Renaud |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2007/0016200 A1 | 1/2007 | Jackson |
| 2007/0032162 A1 | 2/2007 | Jackson |
| 2007/0049932 A1 | 3/2007 | Richelsoph |
| 2007/0049933 A1 | 3/2007 | Ahn |
| 2007/0055239 A1 | 3/2007 | Sweeney |
| 2007/0055240 A1 | 3/2007 | Matthis |
| 2007/0055241 A1 | 3/2007 | Matthis |
| 2007/0055244 A1 | 3/2007 | Jackson |
| 2007/0078460 A1 | 4/2007 | Frigg |
| 2007/0083201 A1 | 4/2007 | Jones |
| 2007/0088357 A1 | 4/2007 | Johnson |
| 2007/0093818 A1 | 4/2007 | Biedermann |
| 2007/0093827 A1 | 4/2007 | Warnick |
| 2007/0118123 A1 | 5/2007 | Strausbaugh |
| 2007/0123860 A1 | 5/2007 | Francis |
| 2007/0123862 A1 | 5/2007 | Warnick |
| 2007/0123870 A1 | 5/2007 | Jeon |
| 2007/0149973 A1 | 6/2007 | Clement |
| 2007/0167949 A1 | 7/2007 | Altarac |
| 2007/0173819 A1 | 7/2007 | Sandlin |
| 2007/0173825 A1 | 7/2007 | Sharifi-Mehr |
| 2007/0173829 A1 | 7/2007 | Drewry |
| 2007/0173833 A1 | 7/2007 | Butler |
| 2007/0213720 A1 | 9/2007 | Gordon |
| 2007/0213721 A1 | 9/2007 | Markworth |
| 2007/0213723 A1 | 9/2007 | Markworth |
| 2007/0233062 A1 | 10/2007 | Berry |
| 2007/0233090 A1 | 10/2007 | Naifeh |
| 2007/0233119 A1 | 10/2007 | Markworth |
| 2007/0265621 A1 | 11/2007 | Matthis |
| 2007/0270808 A1 | 11/2007 | Drewry |
| 2007/0270809 A1 | 11/2007 | Drewry |
| 2007/0270810 A1 | 11/2007 | Sanders |
| 2007/0270842 A1 | 11/2007 | Bankoski |
| 2007/0288009 A1 | 12/2007 | Brown |
| 2008/0021464 A1 | 1/2008 | Morin |
| 2008/0027436 A1 | 1/2008 | Cournoyer |
| 2008/0033434 A1 | 2/2008 | Boomer |
| 2008/0039844 A1 | 2/2008 | Jackson |
| 2008/0045955 A1 | 2/2008 | Berrevoets |
| 2008/0051780 A1 | 2/2008 | Vaidya |
| 2008/0077143 A1 | 3/2008 | Shluzas |
| 2008/0091204 A1 | 4/2008 | Kuiper |
| 2008/0091213 A1 | 4/2008 | Jackson |
| 2008/0109039 A1 | 5/2008 | Michielli |
| 2008/0132953 A1 | 6/2008 | Carbone |
| 2008/0140075 A1 | 6/2008 | Ensign |
| 2008/0154277 A1 | 6/2008 | Machalk |
| 2008/0161859 A1 | 7/2008 | Nilsson |
| 2008/0172093 A1 | 7/2008 | Nilsson |
| 2008/0177260 A1 | 7/2008 | Mckinley |
| 2008/0177315 A1 | 7/2008 | Usher |
| 2008/0177323 A1 | 7/2008 | Null |
| 2008/0183214 A1 | 7/2008 | Copp |
| 2008/0208256 A1 | 8/2008 | Thramann |
| 2008/0249576 A1 | 10/2008 | Hawkes |
| 2008/0255617 A1 | 10/2008 | Cho |
| 2008/0269742 A1 | 10/2008 | Levy |
| 2008/0306525 A1 | 12/2008 | Mitchell |
| 2008/0306534 A1 | 12/2008 | Winslow |
| 2008/0306535 A1 | 12/2008 | Winslow |
| 2008/0306540 A1 | 12/2008 | Mitchell |
| 2008/0306541 A1 | 12/2008 | Mitchell |
| 2008/0306542 A1 | 12/2008 | Mitchell |
| 2008/0312692 A1 | 12/2008 | Brennan |
| 2009/0005814 A1 | 1/2009 | Miller |
| 2009/0005815 A1 | 1/2009 | Ely |
| 2009/0043338 A1 | 2/2009 | Laager |
| 2009/0062860 A1 | 3/2009 | Frasier |
| 2009/0071273 A1 | 3/2009 | Velasco |
| 2009/0082812 A1 | 3/2009 | Lewis |

(56) References Cited

U.S. PATENT DOCUMENTS

| | | |
|---|---|---|
| 2009/0125065 A1 | 5/2009 | Laager |
| 2009/0138044 A1 | 5/2009 | Bergeron |
| 2009/0157125 A1 | 6/2009 | Hoffman |
| 2009/0198280 A1 | 8/2009 | Spratt |
| 2009/0204155 A1 | 8/2009 | Aschmann |
| 2009/0216277 A1 | 8/2009 | Tornier |
| 2009/0306721 A1 | 12/2009 | Kirschman |
| 2009/0318968 A1 | 12/2009 | Duggal |
| 2010/0094306 A1 | 4/2010 | Chang |
| 2010/0094345 A1 | 4/2010 | Saidha |
| 2010/0094346 A1 | 4/2010 | Matityahu |
| 2010/0094349 A1 | 4/2010 | Hammer |
| 2010/0145394 A1 | 6/2010 | Harvey |
| 2010/0160977 A1 | 6/2010 | Gephart |
| 2010/0160981 A1 | 6/2010 | Butler |
| 2010/0191289 A1 | 7/2010 | Ludwig |
| 2010/0198260 A1 | 8/2010 | Gabelberger |
| 2010/0204733 A1 | 8/2010 | Rathbun |
| 2010/0204735 A1 | 8/2010 | Gephart |
| 2010/0211100 A1 | 8/2010 | Mack |
| 2010/0234891 A1 | 9/2010 | Freeman |
| 2010/0268279 A1 | 10/2010 | Gabelberger |
| 2010/0324599 A1 | 12/2010 | Montello |
| 2011/0034957 A1 | 2/2011 | Biedermann |
| 2011/0046675 A1 | 2/2011 | Barrus |
| 2011/0066189 A2 | 3/2011 | Biedermann |
| 2011/0071569 A1 | 3/2011 | Black |
| 2011/0087288 A1 | 4/2011 | Stevenson . |
| 2011/0106178 A1 | 5/2011 | Schwab |
| 2011/0125195 A1 | 5/2011 | Biedermann |
| 2011/0178559 A1 | 7/2011 | Barry |
| 2011/0184462 A1 | 7/2011 | Gil |
| 2011/0319943 A1 | 12/2011 | Donahoe |
| 2012/0035663 A1 | 2/2012 | Jackson |
| 2012/0039566 A1 | 2/2012 | Ruiz Cruz |
| 2012/0071926 A1 | 3/2012 | Jani |
| 2012/0101529 A1 | 4/2012 | Ludwig |
| 2012/0123477 A1 | 5/2012 | Landry |
| 2012/0130436 A1 | 5/2012 | Haskins |
| 2012/0226317 A1 | 9/2012 | Potash |
| 2012/0239090 A1 | 9/2012 | Abdou |

FOREIGN PATENT DOCUMENTS

| | | |
|---|---|---|
| CA | 2045502 | 5/1991 |
| DE | 3841008 | 6/1990 |
| DE | 9004960 | 8/1991 |
| DE | 19950075 | 4/2001 |
| DE | 10055888 | 4/2002 |
| DE | 102009060396 | 6/2011 |
| EP | 0283373 | 9/1988 |
| EP | 1743585 | 12/2007 |
| FR | 2624720 | 6/1989 |
| WO | WO-9513754 | 5/1995 |
| WO | WO-9832386 | 7/1998 |
| WO | WO-9852482 | 11/1998 |
| WO | WO-2006025919 | 3/2006 |
| WO | WO-2006029373 | 3/2006 |
| WO | WO-2007061960 | 5/2007 |
| WO | WO-2007130007 | 11/2007 |
| WO | WO-2008013892 | 1/2008 |
| WO | WO-2009012247 | 1/2009 |
| WO | WO-2009055747 | 4/2009 |
| WO | WO-2010045219 | 4/2010 |
| WO | WO-2011057178 | 5/2011 |

OTHER PUBLICATIONS

Dipreta, "The Iliac Nail/Screw in a Modified Galveston Technique for Sacropelvic Fixation", *Am. Acad. of Ortho. Surg.*, $67^{th \; mtg., \; PE184}$, (Mar. 19, 2000), 1 pg.

Ebrahim, "Posterior Lateral Mass Screw Fixation: Anatomic and Radiographic Considerations", *U.P.O.J.* vol. 12 (Spring 1999), 66-72.

Erickson, "Biomechanical Assessment of Conventional Unit Rod Fixation Versus a Unit Rod Pedicle Screw Construct", *Spine*, vol. 29, No. 12, (2004), 1314-1319.

Pham, "Upper cervical spine surgery in rheumatoid arthritis: retrospective study of 30 patients followed for two years or more after Cotrel-Dubousset instrumentation", *Joint Bone Spine*, 67 (2000), 434-440.

Sanders, "Treating, managing spinal deformity in young patients", Orthopedics Today (Jul. 2001), 12 pgs.

Spiegel, "Anterior instrumentation in the Treatment of Scolisosis" 1998), *U.P.O.J.*, vol. 11, (Spring 1998), 19-26.

Synthes Spine, "The CerviFix System Including the StarLock Components," 2000, 16 pages.

Wood, "Torsional Rigidity of Scoliosis Constructs", *Spine*, vol. 25, No. 15, (2000), 1893-1898.

SURGICAL FIXATION SYSTEM AND RELATED METHODS

CROSS REFERENCE TO RELATED APPLICATIONS

The present application is a continuation of U.S. patent application Ser. No. 13/453,885, filed Apr. 23, 2012, now pending, which is a continuation of U.S. patent application Ser. No. 13/315,082, filed Dec. 8, 2011, now abandoned, which is a continuation of U.S. patent application Ser. No. 13/185,434, filed Jul. 18, 2011, now abandoned, which is a continuation of U.S. patent application Ser. No. 13/037,194, filed Feb. 28, 2011, now abandoned, which is a continuation of U.S. patent application Ser. No. 12/906,685, filed Oct. 18, 2010, now abandoned, which is a continuation of U.S. patent application Ser. No. 12/794,016, filed Jun. 4, 2010, now abandoned, which is a continuation of U.S. patent application Ser. No. 12/581,790, filed Oct. 19, 2009, now abandoned, which is a continuation of U.S. patent application Ser. No. 12/396,332, filed Mar. 2, 2009, now abandoned, which claims the benefit of priority under 35 U.S.C. §119(e) from U.S. Provisional Patent Application Ser. No. 61/032,768, filed on Feb. 29, 2008, the entire contents of which is hereby expressly incorporated by reference into this disclosure as if set forth fully herein.

BACKGROUND OF THE INVENTION

I. Field of the Invention

The present invention relates generally to the field of spinal fixation surgery, and more specifically to posterior cervical fixation assemblies and techniques for securing an orthopedic rod to a spine.

II. Background

The spinal column is a highly complex system of bones and connective tissues that provides support for the body and protects the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies.

There are many types of spinal column disorders including scoliosis (abnormal lateral curvature of the spine), kyphosis (abnormal forward curvature of the spine), excess lordosis (abnormal backward curvature of the spine), spondylothesis (forward displacement of one vertebra over another), and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

Surgical techniques commonly referred to as spinal fixation use surgical implants for fusing together and/or mechanically immobilizing two or more vertebral bodies of the spinal column. Spinal fixation may also be used to alter the alignment of adjacent vertebral bodies relative to one another so as to change the overall alignment of the spinal column. Such techniques have been used effectively to treat the above-described conditions and, in most cases, to relieve pain.

One spinal fixation technique involves immobilizing the spine using orthopedic stabilizing rods, commonly referred to as spine rods, which run generally parallel to the spine. This may be accomplished by exposing the spine posteriorly, and fastening bone screws and/or hooks to the vertebral bodies. The screws and/or hooks are generally placed two per vertebra and serve as anchor points for the spine rods. Clamping or coupling elements adapted for receiving a spine rod therethrough are then used to join the spine rods to the screws or hooks. The aligning influence of the spine rods forces the spinal column to conform to a more desirable shape. In certain instances, the spine rods may be bent to achieve the desired curvature of the spinal column.

There are many disadvantages associated with current spinal fixation devices. For example, many prior art bone fixation devices are less than optimal for capturing spine rods when the coupling elements must be rotated to extreme angles. With such devices, pivotal movement of the anchor portion is limited to an angle of generally no more than 40° (measured from vertical) in any direction. Surgeons have encountered considerable difficulty attempting to insert spinal fixation devices when the coupling elements are out of alignment with one another due to curvature of the spinal column and the different orientation of adjacent pedicles receiving screws. As a result, spine rods must often be bent in multiple planes in order to pass the rods through adjacent coupling elements. This may potentially weaken the overall assembly and results in longer operations and a greater likelihood of complications. Further problems may arise when applying an occipital plate due to the natural curvature of a patient's spine, the difference in relative position of the occiput compared with the vertebral bodies, and the irregular shape and thickness of the occiput.

The occipital-cervical (OC) junction is the most cephalad portion of the spinal column, spanning from the occiput to the C2 vertebra. This bony junction allows for significant mobility while maintaining biomechanical stability. OC instability is a rare disorder with potentially life-threatening consequences. Such instability may cause disabling pain, cranial nerve dysfunction, paralysis, or even sudden death. One common effect of OC instability includes dislocation of the atlantooccipital (i.e. C1-occiput) joint and complex fractures of the C1 and C2 vertebrae. OC fusion is often warranted when the OC junction is rendered unstable. OC fixation procedures to stabilize the OC junction are a challenge to spine surgeons. Due mostly to the neighboring anatomy and relatively difficult occipital bone purchase, multiple attachment points to the occipital bone are generally required to increase construct rigidity. Moreover, the instrumentation utilized must accommodate the anatomic structures and satisfy the biomechanical needs and the kinematics of the area. Current systems are generally rigid posterior fixation systems using rods/screws or plates, providing biomechanical stability and generally high rates of fusion. However, current OC fixation systems have limitations in the cephalad part of the construct. Part of the problem is that the occiput does not easily accommodate instrumentation, and the area available for the fixation of implants is limited. Occipital screws required in current techniques may also be associated with the potential for intracranial injuries.

The occipital condyles are the only osseous structures that support the head, with a length generally ranging from 16.7 mm to 30.6 mm, a width generally ranging from 6.5 mm to 15.8 mm, and a height generally ranging from 5.8 mm to 18.2 mm. The condyles are generally oval shaped and converge ventrally with a sagittal angle ranging from 10 to 54 degrees. The variability in the anatomic parameters requires a careful radiologic analysis of the condyles before screw placement. The hypoglossal canal, which passes above the occipital condyle, is surrounded by the jugular tubercle superiorly, the jugular foramen superolaterally, the sigmoid sinus laterally, and the occipital condyle inferiorly, with the axis 45 degrees in the axial plane and directed slightly superiorly. The mean distance from hypoglossal canal to the inferior border of the condyle is 11.5 mm which allows enough room to safely place a condylar screw. Moreover, the canal offers additional protection to the hypoglossal nerve as it is surrounded by cortical bone. The proximity of neurovascular structures during the surgical exposure is another anatomic consideration that must be taken into account prior to performing any occipital procedure.

The present invention is directed at overcoming, or at least improving upon, the disadvantages of the prior art.

SUMMARY OF THE INVENTION

The present invention accomplishes this goal by providing a method for occipito-cervical fixation using condyles as fixation points for an OC fusion. The goals of the methods and instrumentation described herein are to provide immediate stability, improve fusion rates, diminish the need for postoperative external immobilization, and decrease rehabilitation time. The method of performing spinal fixation surgery described herein generally involves installing a plurality of spinal rods and polyaxial screws along at least a portion of the posterior of the spinal column to fix the vertebrae in a desired spatial relationship and aid in spinal fusion, if necessary. Although the method is shown and described herein as using screws to fix the rods to bone, alternative fixation mechanisms may be utilized without departing from the scope of the present invention, including but not limited to hooks, clamps, staples, sutures, and the like.

The first step in the method of the present invention is to create an operative field for the surgical target site. Generally, access to the surgical target site is performed by exposing the occiput and cervical spine by methods known in the art. Attention may then be focused on the foramen magnum. Using curettes (for example), the atlantooccipital membrane is gently dissected from the foramen magnum laterally until the occipital condyle is reached. At this point, the dissection continues laterally, maintaining bone contact to prevent injury to the horizontal segment of the vertebral artery along the condylar fossa, until the posterior condylar foramen and emissary vein are identified. The condylar foramen and vein represent the lateral extent of the dissection. At this point, the operative field is established and the surgical fixation procedure may continue.

The next steps of the method involve screw placement along the posterior aspect of the spine. To accomplish this step, polyaxial screws are placed in the C1 and C2 vertebrae. Screws may be any size appropriate to achieve fixation, and may vary in the size necessary depending on the placement of the screw and particular vertebra involved. In the example described herein, the screws are approximately 3.5 mm in diameter. Screw length may range between 22-44 mm, (e.g. 34 to 44 mm for transarticular C1-C2 screws placement, 28 to 34 mm for C1 lateral mass screws, and 22 to 24 mm for C2 pedicle screws). Inserting the cervical screws first provides useful information about the axial location of the occipital condyles.

A this point the condyle screws may be inserted. The condylar entry point (CEP) may be defined using a combination of radiographic and anatomic landmarks. Generally the CEP is located 4 to 5-mm lateral to the posteromedial edge of the condyle at its junction with the occipital bone at the condylar fossa. The condylar fossa is defined laterally by the condylar emissary vein and inferiorly by the horizontal segment of the vertebral artery, which is cushioned by a dense venous plexus. Pilot holes may be made at the entry point using an awl with slight rostral angulation to avoid injury to the horizontal segment of the vertebral artery. The pilot hole is then drilled in a convergent trajectory with 12 to 22 degrees of medial angulation and 5-degrees cranial angulation in the sagittal plane with the tip of the drill directed toward the basion. The drilling may be accomplished with guidance from intraoperative landmarks and lateral fluoroscopic imaging, advancing slowly until the anterior cortical edge of the condyle is breached. The hole is then tapped, and a 3.5-mm polyaxial condyle screw of an appropriate length (for example 30 to 32 mm) is inserted bicortically into the occipital condyle. By way of example only, condyle screw may include a threaded portion and an unthreaded portion. The unthreaded portion may have any length appropriate for the procedure, however approximately 11 to 13 mm of the unthreaded portion of the screw remains exposed from the condyle, allowing the polyaxial portion of the screw to lie above the posterior arch of C1 vertebra, minimizing any chance of irritation of the vertebral artery by the spinal rods. Hardware position may be confirmed by fluoroscopy after fixation.

Using the trajectory described above, upon completion of the technique described herein the screws should be located inside the condyles with complete integrity of all osseous elements. Proper condyle screw insertion should create no fractures, and the integrity of the hypoglossal canal should also be maintained.

The CEP corresponds to the midcondylar area, approximately 4 to 5 mm lateral to the foramen magnum on the axial plane and 1 to 2-mm rostral to the atlantooccipital joint. There is flexibility in terms of the screw angulation relative to the axial plane that allows good bone purchase. This angulation may range from 12 to 22 degrees (mean of 17 degrees). The preferable superior screw angulation in the sagittal plane is 5 degrees (limited by the angulation of the occipital bone). Condyle screws may have a length of approximately 30-32 mm, including a threaded purchase region ranging from 20 to 24 mm to obtain sufficient bicortical purchase. In order to keep the polyaxial head of the condyle screw posterior enough to avoid compression of the vertebral artery and facilitate attachment of the rods 26, it may be desirable to allow an overhang of the posterior arch of C1 vertebra ranging from 11 to 13 mm.

After placement of the condyle screws and cervical screws, the spinal rod may be affixed to the screws. Using condyle screws having 20 to 24 mm of bicortical condylar purchase as described herein may decrease complications related to screw breakage, pullout, and/or loosening and diminish the need for multiple occipital fixation points. Furthermore, the creation of two parallel constructs aligned with the lateral masses has the advantages associated with the lateral occipital fixation techniques and may provide a more sound biomechanical construct.

Generally, for OC fixation, rod and screw devices may have significantly reduced stiffness in flexion-extension and allow a greater range of motion, compared with plate and screw systems. This difference may be due to a greater area moment of inertia of the rod rather than variation in placement of occipital screws or locking of the implant. In any event, decreasing the length of the lever arm of the construct, increasing the length of the screws, and use of the condyles as fixation points may provide for a more rigid OC construct, without the need for increased rod diameter or multiple attachment points. Thus, the benefits of low profile modular craniocervical fixation are retained while the complications associated with occipital screw placement are reduced. Furthermore, a midline or lateral occipital screw technique can be used for additional or supplemental fixation points.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The method of performing spinal fixation surgery disclosed herein boasts a variety of inventive features and components that warrant patent protection, both individually and in combination.

Figure 1:
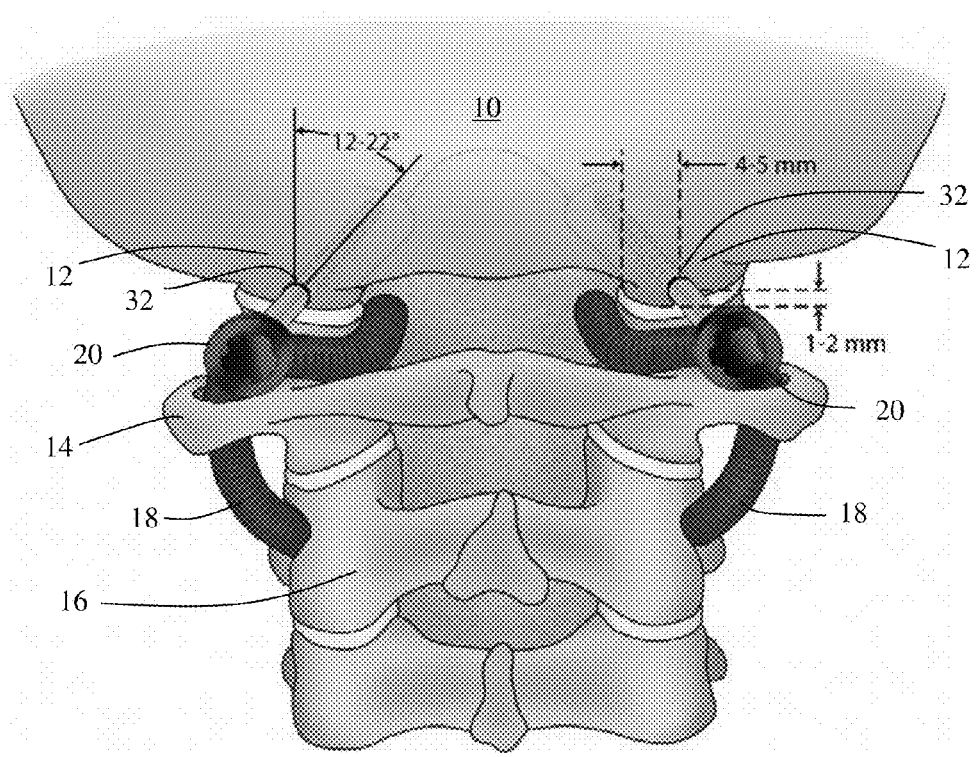
FIG. 1 is a posterior view of the occipito-cervical region of the spine illustrating condyle screws placed according to one embodiment of the method of the present invention.

FIG. 1 illustrates an example of placement of a pair of condyle screws 20 as part of a method of performing spinal fixation surgery according to one embodiment of the present invention. Specifically, FIG. 1 provides a posterior view of the occipito-cervical region of the spine, including the occiput 10, condyles 12, C1 (i.e. "atlas") vertebra 14, and C2 (i.e. "axis") vertebra 16. The method of performing spinal fixation surgery described herein generally involves installing a plurality of spinal rods and polyaxial screws along at least a portion of the posterior of the spinal column to fix the vertebrae in a desired spatial relationship and aid in spinal fusion, if necessary. Although the method is shown and described herein as using screws to fix the rods to bone, alternative fixation mechanisms may be utilized without departing from the scope of the present invention, including but not limited to hooks, clamps, staples, sutures, and the like.

The first step in the method of the present invention is to create an operative field for the surgical target site. Generally, access to the surgical target site is performed by exposing the occiput and cervical spine by methods known in the art. Attention may then be focused on the foramen magnum. Using curettes (for example), the atlantooccipital membrane is gently dissected from the foramen magnum laterally until the occipital condyle is reached. At this point, the dissection continues laterally, maintaining bone contact to prevent injury to the horizontal segment of the vertebral artery along the condylar fossa, until the posterior condylar foramen and emissary vein are identified. The condylar foramen and vein represent the lateral extent of the dissection. At this point, the operative field is established and the surgical fixation procedure may continue.

Figure 3:
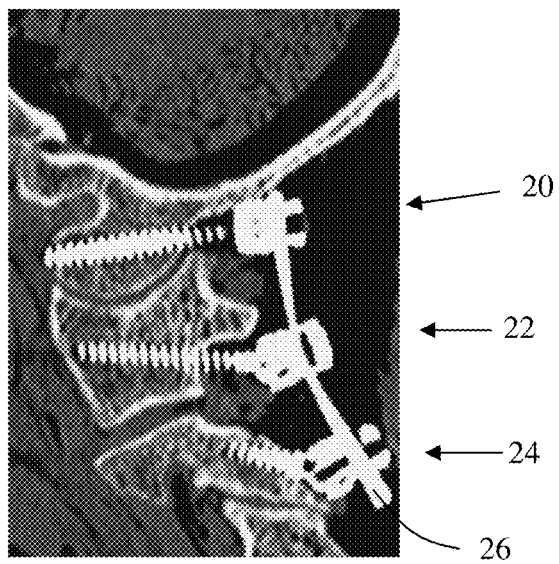
FIG. 3 is a side cross-sectional view of the occipito-cervical region of the spine shown in FIG. 1.
Figure 4:
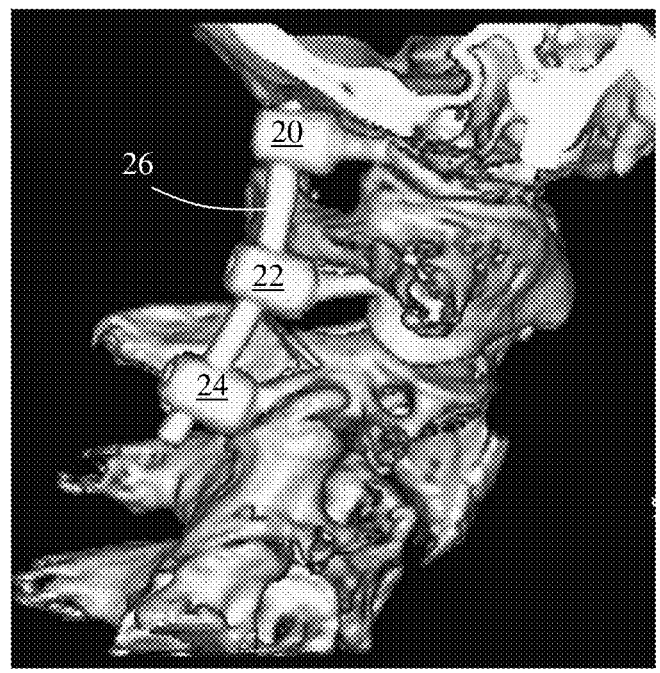
FIG. 4 is a side view of the occipito-cervical region of the spine shown in FIG. 1.

The next steps of the method involve screw placement along the posterior aspect of the spine. To accomplish this step, polyaxial screws 22, 24 are placed in the C1 and C2 vertebrae 12, 14, respectively, as shown in FIGS. 3 and 4. Screws 22, 24 may be any size appropriate to achieve fixation, and may vary in the size necessary depending on the placement of the screw and particular vertebra involved. In the example described herein, the screws are approximately 3.5 mm in diameter. Screw length may range between 22-44 mm, (e.g. 34 to 44 mm for transarticular C1-C2 screws placement, 28 to 34 mm for C1 lateral mass screws, and 22 to 24 mm for C2 pedicle screws). Inserting the cervical screws first provides useful information about the axial location of the occipital condyles 12.

Figure 2:
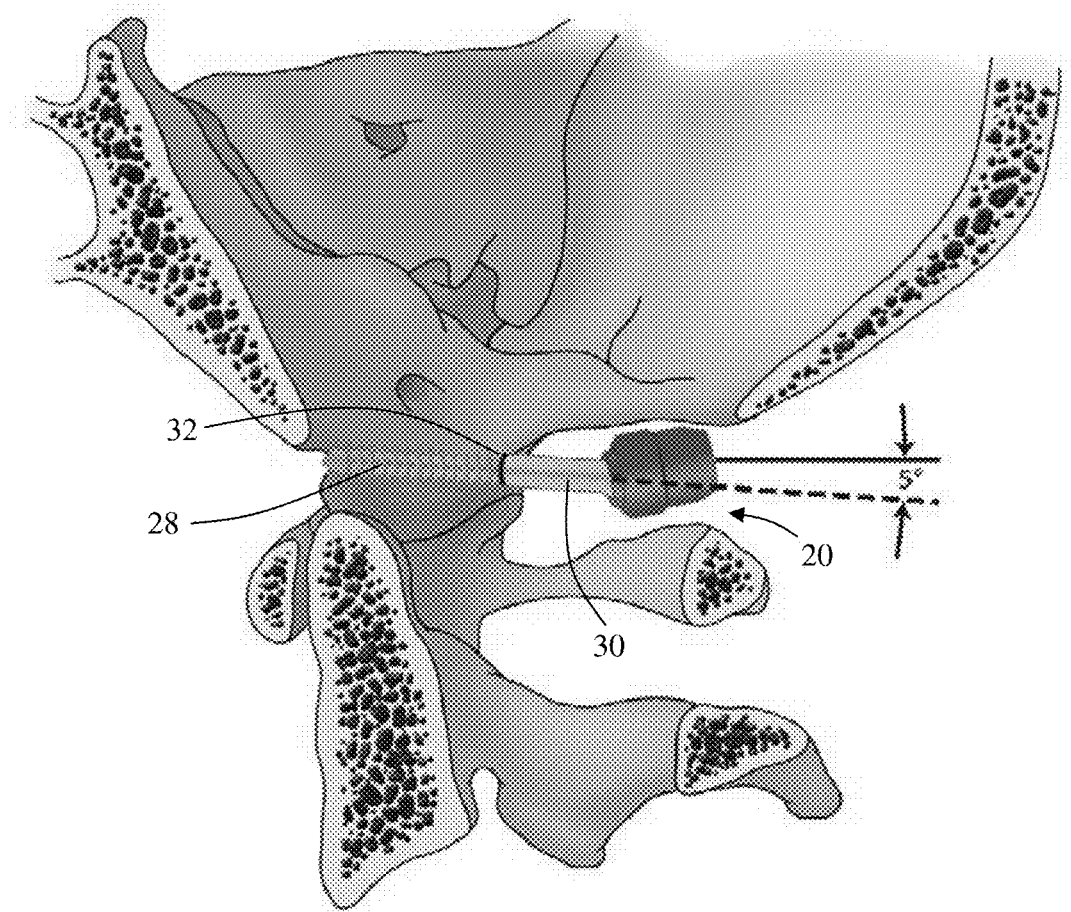
FIG. 2 is a side view of the occipito-cervical region of the spine shown in FIG. 1.

At this point the condyle screws 20 may be inserted. Referring again to FIG. 1, the condylar entry point (CEP) 32 may be defined using a combination of radiographic and anatomic landmarks. Generally the CEP 32 is located 4 to 5-mm lateral to the posteromedial edge of the condyle 12 at its junction with the occipital bone at the condylar fossa. The condylar fossa is defined laterally by the condylar emissary vein and inferiorly by the horizontal segment of the vertebral artery 18, which is cushioned by a dense venous plexus. Pilot holes may be made at the entry point using an awl with slight rostral angulation to avoid injury to the horizontal segment of the vertebral artery 18. The pilot hole is then drilled in a convergent trajectory with 12 to 22 degrees of medial angulation and 5-degrees cranial angulation in the sagittal plane (as illustrated in FIGS. 1 and 2) with the tip of the drill directed toward the basion. The drilling may be accomplished with guidance from intraoperative landmarks and lateral fluoroscopic imaging, advancing slowly until the anterior cortical edge of the condyle is breached. The hole is then tapped, and a 3.5-mm polyaxial condyle screw 20 of an appropriate length (for example 30 to 32 mm) is inserted bicortically into the occipital condyle 12. By way of example only, condyle screw 20 may include a threaded portion 28 and an unthreaded portion 30. The unthreaded portion 30 may have any length appropriate for the procedure, however approximately 11 to 13 mm of the unthreaded portion of the screw remains exposed from the condyle, allowing the polyaxial portion of the screw to lie above the posterior arch of C1 vertebra 14, minimizing any chance of irritation of the vertebral artery 18 by the spinal rods 26 (FIGS. 3-4). Hardware position may be confirmed by fluoroscopy after fixation.

Using the trajectory described above, upon completion of the technique described herein the screws should be located inside the condyles 12 with complete integrity of all osseous elements. Proper condyle screw 20 insertion should create no fractures, and the integrity of the hypoglossal canal should also be maintained.

Figure 5:
FIG. 5 is a top cross-sectional view of the occipito-cervical region of the spine shown in FIG. 1.

As previously discussed, the CEP 32 corresponds to the midcondylar area, approximately 4 to 5 mm lateral to the foramen magnum on the axial plane and 1 to 2-mm rostral to the atlantooccipital joint. There is flexibility in terms of the screw angulation relative to the axial plane that allows good bone purchase. This angulation may range from 12 to 22 degrees (mean of 17 degrees) (FIGS. 1 and 5). As shown in FIG. 2, the preferable superior screw angulation in the sagittal plane is 5 degrees (limited by the angulation of the occipital bone). Condyle screws 20 may have a length of approximately 30-32 mm, including a threaded purchase region ranging from 20 to 24 mm to obtain sufficient bicortical purchase. In order to keep the polyaxial head of the condyle screw 20 posterior enough to avoid compression of the vertebral artery 18 and facilitate attachment of the rods 26 (FIGS. 3-4), it may be desirable to allow an overhang of the posterior arch of C1 vertebra 14 ranging from 11 to 13 mm.

After placement of the condyle screws 20 and cervical screws 22, 24, the spinal rod 26 may be affixed to the screws as shown in FIGS. 3 and 4. This is accomplished by placing the rod 26 within the polyaxial heads of the condyle screw 20 and the polyaxial screws 22, 24. The rod 26 may be bent to a desired angulation in order to facilitate engagement with the screws 20, 22, 24.

Using condyle screws having 20 to 24 mm of bicortical condylar purchase as described herein may decrease complications related to screw breakage, pullout, and/or loosening and diminish the need for multiple occipital fixation points. Furthermore, the creation of 2 parallel constructs aligned with the lateral masses has the advantages associated with the lateral occipital fixation techniques and may provide a more sound biomechanical construct.

Generally, for OC fixation, rod and screw devices may have significantly reduced stiffness in flexion-extension and allow a greater range of motion, compared with plate and screw systems. This difference may be due to a greater area moment of inertia of the rod rather than variation in placement of occipital screws or locking of the implant. In any event, decreasing the length of the lever arm of the construct, increasing the length of the screws, and use of the condyles as fixation points may provide for a more rigid OC construct, without the need for increased rod diameter or multiple attachment points. Thus, the benefits of low profile modular craniocervical fixation are retained while the complications associated with occipital screw placement are reduced. Furthermore, a midline or lateral occipital screw technique can be used for additional or supplemental fixation points.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method of performing spinal fixation surgery, comprising:
    (a) creating an operative corridor to a surgical target site, the surgical target site at least partially comprising an occipito-cervical region of a human spine, the occipito-cervical region including an occiput, a pair of occipital condyles, and at least two cervical vertebrae;
    (b) implanting a plurality of vertebral fixation elements in a posterior aspect of at least one of said cervical vertebrae;
    (c) implanting a condylar fixation element in each of said occipital condyles;
    (d) implanting at least one rod member, said rod member attached to one of said condylar fixation elements and at least one of said vertebral fixation elements;
    (e) locking said spinal rod to said condylar fixation element and said at least one vertebral fixation element; and
    (f) closing said operative corridor.

2. The method of claim 1, wherein said posterior aspect comprises at least one of an articular process, a lateral mass, and a pedicle.

3. The method of claim 1, wherein said vertebral fixation elements comprise polyaxial bone screws each having a tulip portion for receiving said spinal rod and a threaded element for providing purchase within bone.

4. The method of claim 1, wherein said at least two cervical vertebrae comprise the C1 and C2 cervical vertebrae.

5. The method of claim 1, wherein said condylar fixation elements are placed in a range of approximately 4-5 millimeters lateral to the posteromedial edge of the occipital condyle at a junction with the occipital bone at the condylar fossa.

6. The method of claim 1, wherein said condylar fixation elements are implanted in a convergent trajectory.

7. The method of claim 6, wherein said trajectory includes a range of approximately 12 to 22 degrees of medial angulation.

8. The method of claim 6, wherein said trajectory includes approximately 5 degrees of cranial angulation in the sagittal plane.

9. The method of claim 1, wherein said condylar fixation element is a bone screw having a polyaxial tulip portion and an elongated shaft having a threaded portion and an unthreaded portion.

10. The method of claim 9, wherein after implantation of said condylar fixation elements within said occipital condyle, a range of approximately 11 to 13 millimeters of said unthreaded portion remains exposed from said occipital condyle.

11. The method of claim 9, wherein after implantation of said condylar fixation elements within said occipital condyle, said polyaxial tulip portion of said condylar fixation element is positioned above the arch of the C1 cervical vertebra.

12. The method of claim 9, wherein said condylar fixation element includes a threaded portion having a length ranging from 20 to 24 millimeters.

* * * * *